(12) United States Patent
Lenser

(10) Patent No.: US 9,517,887 B2
(45) Date of Patent: Dec. 13, 2016

(54) APPARATUS AND METHOD FOR CONVEYING ABSORBENT ARTICLES

(71) Applicant: The Procter & Gamble Company, Cincinnati, OH (US)

(72) Inventor: Todd Douglas Lenser, Liberty Township, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 120 days.

(21) Appl. No.: 14/549,613

(22) Filed: Nov. 21, 2014

(65) Prior Publication Data

US 2015/0158673 A1   Jun. 11, 2015

Related U.S. Application Data

(60) Provisional application No. 61/912,116, filed on Dec. 5, 2013.

(51) Int. Cl.
*B65G 15/58* (2006.01)
*B65G 21/20* (2006.01)
(Continued)

(52) U.S. Cl.
CPC ......... *B65G 15/58* (2013.01); *A61F 13/15764* (2013.01); *B65G 13/07* (2013.01);
(Continued)

(58) Field of Classification Search
CPC ..... B65G 15/58; B65G 21/2036; B65G 23/06; B65G 13/07
(Continued)

(56) References Cited

U.S. PATENT DOCUMENTS 3,735,976 A   5/1973   Watson
3,860,003 A   1/1975   Buell
(Continued)

FOREIGN PATENT DOCUMENTS

CN   201 301 158 Y   9/2009
JP      S4923970 U   2/1974
(Continued)

OTHER PUBLICATIONS

U.S. Appl. No. 12/459,603, filed Nov. 21, 2014, Todd Douglas Lenser.

(Continued)

*Primary Examiner* — Leslie A Nicholson, III
(74) *Attorney, Agent, or Firm* — Sarah M. DeCristofaro

(57) ABSTRACT

An apparatus and method for conveying absorbent articles may utilize a conveyor including a vacuum source in fluid connection with a deck. The deck may include a channel. The conveyor may also include a belt including a first surface, an opposing second surface, and an aperture. The second surface of the belt may be in facing relationship with the deck such that the aperture is aligned with the channel. A first row of angled teeth and a second row of straight teeth may be connected with the second surface of the belt. The first row of angled teeth and the second row of straight teeth mesh with a first gear member and a second gear member, respectively. The first and second gear members may be attached to an axle member such that the first gear member and the second gear member rotate with the axle member advancing the belt.

4 Claims, 12 Drawing Sheets

(51) Int. Cl.
  *B65G 13/07* (2006.01)
  *B65G 23/06* (2006.01)
  *B65G 23/04* (2006.01)
  *A61F 13/15* (2006.01)
  *B65H 29/24* (2006.01)
  *B65H 5/22* (2006.01)

(52) U.S. Cl.
  CPC ......... *B65G 21/2036* (2013.01); *B65G 23/04* (2013.01); *B65G 23/06* (2013.01); *B65H 5/224* (2013.01); *B65H 29/242* (2013.01); *B65H 2403/45* (2013.01); *B65H 2404/251* (2013.01)

(58) Field of Classification Search
  USPC .................. 198/465.3, 471.1, 689.1, 781.01, 791,198/832, 834
  See application file for complete search history.

(56) References Cited

U.S. PATENT DOCUMENTS

| | | | |
|---|---|---|---|
| 4,610,678 A | 9/1986 | Weisman et al. | |
| 4,673,402 A | 6/1987 | Weisman et al. | |
| 4,695,278 A | 9/1987 | Lawson | |
| 4,704,115 A | 11/1987 | Buell | |
| 4,795,454 A | 1/1989 | Dragoo | |
| 4,834,735 A | 5/1989 | Alemany et al. | |
| 4,888,231 A | 12/1989 | Angstadt | |
| 4,909,803 A | 3/1990 | Aziz et al. | |
| 5,020,656 A * | 6/1991 | Faulkner | 198/494 |
| 5,234,097 A * | 8/1993 | Okuyama | 198/434 |
| 5,348,285 A | 9/1994 | Hueser | |
| 5,469,958 A * | 11/1995 | Gruettner et al. | 198/834 |
| 5,553,536 A * | 9/1996 | Van Os | 101/44 |
| 5,562,646 A | 10/1996 | Goldman et al. | |
| 5,599,335 A | 2/1997 | Goldman et al. | |
| 5,628,097 A | 5/1997 | Benson et al. | |
| 5,669,894 A | 9/1997 | Goldman et al. | |
| 5,704,861 A * | 1/1998 | Feuerborn | 474/153 |
| 5,916,661 A | 6/1999 | Benson et al. | |
| 6,107,539 A | 8/2000 | Palumbo et al. | |
| 6,419,072 B2 * | 7/2002 | Kelley | 198/346.1 |
| 6,443,443 B1 | 9/2002 | Hirth et al. | |
| 6,545,197 B1 | 4/2003 | Muller et al. | |
| 6,564,932 B2 * | 5/2003 | Itoh | 198/835 |
| 6,723,035 B2 | 4/2004 | Franklin et al. | |
| 6,776,316 B2 | 8/2004 | Van Eperen et al. | |
| 6,790,798 B1 | 9/2004 | Suzuki et al. | |
| 7,270,631 B2 | 9/2007 | Franklin et al. | |
| 7,569,039 B2 | 8/2009 | Matsuda et al. | |
| 7,681,717 B2 * | 3/2010 | DeGroot | 198/832 |
| 7,810,637 B2 * | 10/2010 | Gundlach | 198/834 |
| 8,042,682 B2 * | 10/2011 | Ertel | 198/834 |
| 2004/0097895 A1 | 5/2004 | Busam et al. | |
| 2004/0158212 A1 | 8/2004 | Ponomarenko et al. | |
| 2005/0107764 A1 | 5/2005 | Matsuda et al. | |
| 2009/0312730 A1 | 12/2009 | LaVon et al. | |
| 2010/0018842 A1 | 1/2010 | Gundlach | |
| 2011/0247747 A1 | 10/2011 | Schneider et al. | |
| 2011/0251038 A1 | 10/2011 | LaVon et al. | |
| 2012/0061015 A1 | 3/2012 | LaVon et al. | |
| 2012/0061016 A1 | 3/2012 | LaVon et al. | |
| 2012/0261455 A1 | 10/2012 | Taylor | |
| 2013/0255861 A1 | 10/2013 | Schneider | |
| 2013/0255862 A1 | 10/2013 | Schneider et al. | |
| 2013/0255863 A1 | 10/2013 | LaVon et al. | |
| 2013/0255864 A1 | 10/2013 | Schneider et al. | |
| 2013/0255865 A1 | 10/2013 | Brown et al. | |
| 2014/0080692 A1 | 3/2014 | Lenser et al. | |

FOREIGN PATENT DOCUMENTS

| | | |
|---|---|---|
| JP | S58 112742 A1 | 7/1983 |
| JP | 2002 054720 A | 2/2002 |

OTHER PUBLICATIONS

PCT/US2014/066730 PCT International Search Report, dated Mar. 13, 2015 9 pages.
Breco flex Co,. L.L.C. High Precision Drive Components Arc-Power Technology.
Eagle Pd Acculinear, Good Year Engineered Products.
Urethane Timing Belts and Pulleys. Gates Mectrol.
Sit Catalog.
PCT/US2014/066729 PCT International Search Report dated Jul. 16, 2015, 9 pages.
PCT/US2014/066729 PCT International Search Report, dated. Sep. 21, 2015, 18 pages.
Breco flex Co,. L.L,C. High Precision Drive Components, Arc-Power Technology, Jun. 2008.
Eagle Pd Acculinear, Good Year Engineered Products, Nov. 2007.
Eagle Pd Brochure, Good Year Engineered Products, Aug. 2005.
Eagle polyurethane belts, Elatech, Apr. 2009.
PCT/US2014/066730 PCT International Search Report, dated Mar. 13, 2015, 9 pages.
Sit Catalog; Elatech, 2010.
Urethane Timing Belts and Pulleys, Gates Mectrol, Nov. 2011.

* cited by examiner

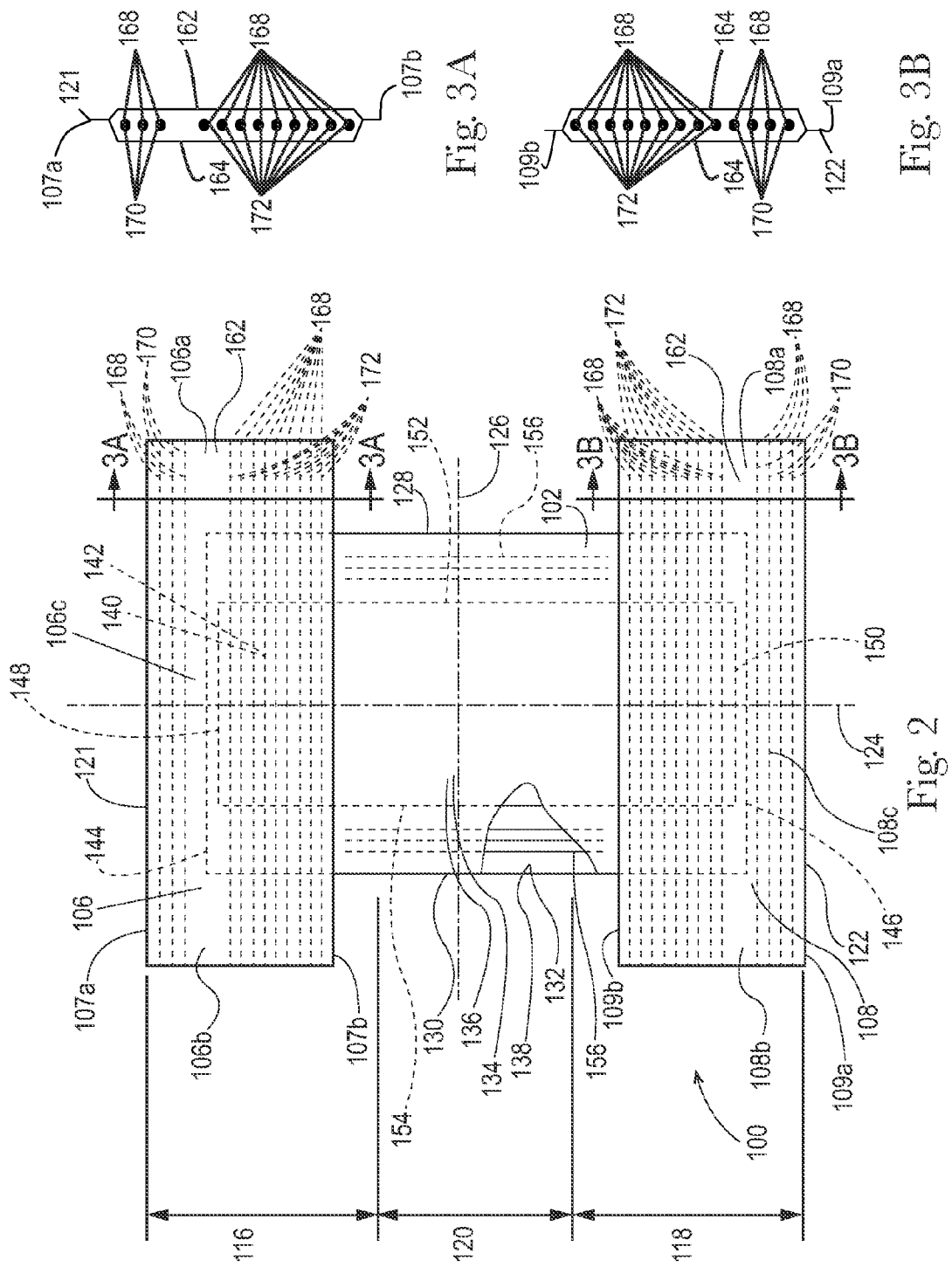

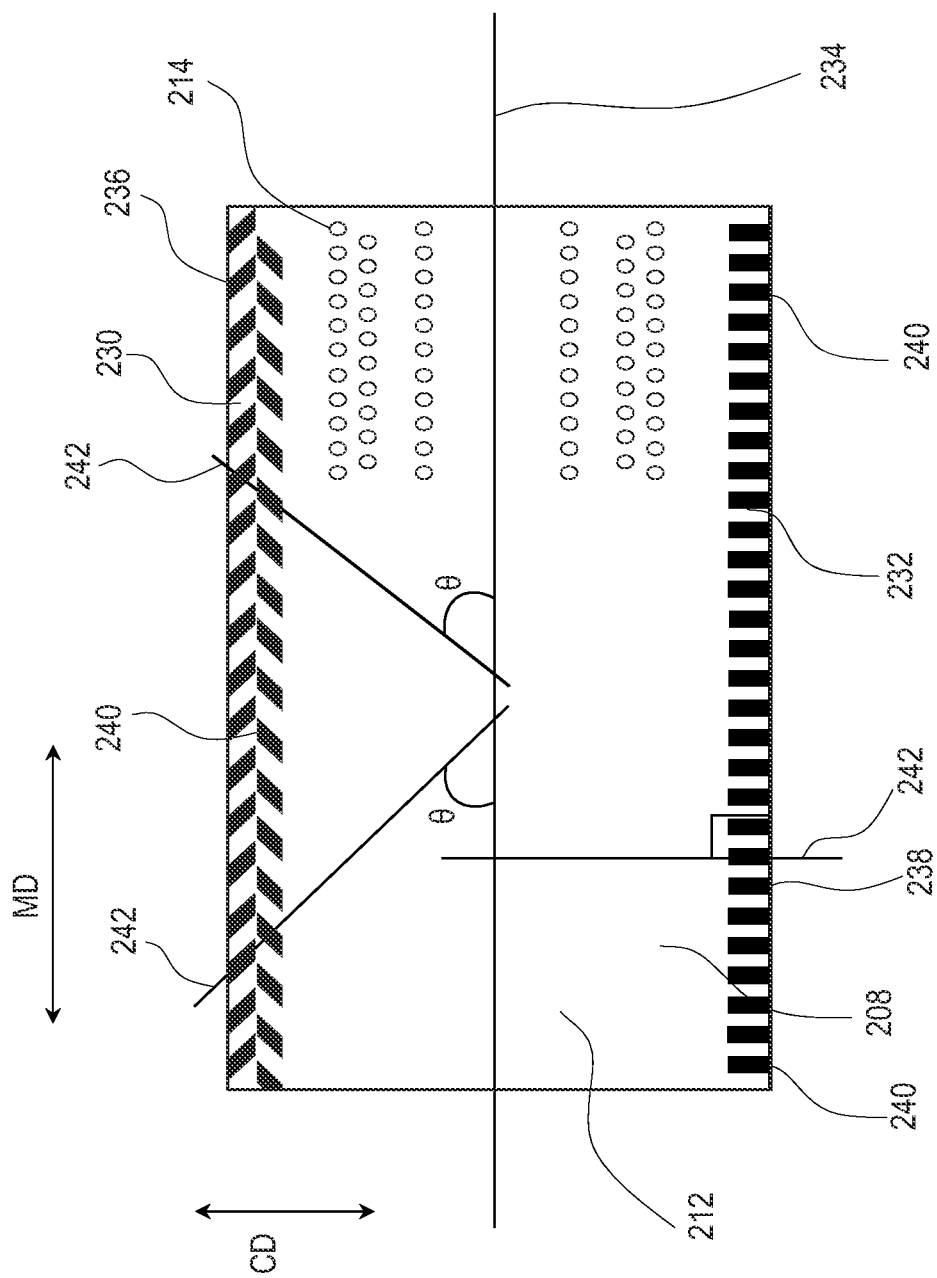

APPARATUS AND METHOD FOR CONVEYING ABSORBENT ARTICLES

CROSS REFERENCE TO RELATED APPLICATION

This application claims the benefit of U.S. Provisional Application No. 61/912,116 filed on Dec. 5, 2013, the substance of which is incorporated herein by reference.

FIELD OF THE INVENTION

The present disclosure relates to an apparatus and method for manufacturing absorbent articles, and more particularly, to an apparatus and method for conveying absorbent articles.

BACKGROUND OF THE INVENTION

Along an assembly line, diapers and various types of other absorbent articles may be assembled by adding components to and otherwise modifying an advancing, continuous web of material. For example, in some processes, advancing webs of material are combined with other advancing webs of material. In other examples, individual components created from advancing webs of material are combined with advancing webs of material, which in turn, are then combined with other advancing webs of material. Webs of material and component parts used to manufacture diapers may include: backsheets, topsheets, absorbent cores, front and/or back ears, fastener components, and various types of elastic webs and components such as leg elastics, barrier leg cuff elastics, and waist elastics. Once the desired component parts are assembled, the advancing web(s) and component parts are subjected to a final knife cut to separate the web(s) into discrete diapers or other absorbent articles. The discrete diapers or absorbent articles may also then be folded and packaged.

During the assembly process, the absorbent article must be conveyed from one operation to the next operation. Due to high manufacturing speeds and an increasing need for control of the article, vacuum conveyors have been used to create a force upon the article as the article is conveyed and/or operated on. More specifically, vacuum conveyors may comprise a belt having a plurality of apertures aligned with slots in a deck. The slots may be fluidly connected with a vacuum source that allows air to be drawn in through the apertures, which in turn, helps hold the article in contact with the belt while being conveyed. However, the use of vacuum conveyors at high manufacturing speeds has presented several problems.

For example, some vacuum conveyors may be equipped with a belt that is driven by gears having straight teeth (or teeth that are oriented perpendicular to the direction of travel) that mesh with correspondingly oriented rows of teeth on the belt. The straight profile of the teeth along with the high speed of the manufacturing line may create a substantial amount of noise. Generally, higher manufacturing speed, larger teeth, and wider tooth profiles are associated with higher noise level. In some configurations, the noise level may become so great that remedial measures must be taken to reduce levels of noise in surrounding areas. For example, conveyors may be required to be housed within a sound insulation structure to protect workers.

Additionally, due to the straight profile of the teeth and the need to manufacture at high speeds, manufacturers may not be able to control the CD position of the belt to a high degree of precision. Other problems that may result from the use of high speed vacuum conveyors may include but are not limited to: mistrack of the belt with respect to the machine frame, mistrack of the apertures in the belt relative to apertures in an apertured deck surface, inability to maintain alignment between the apertures in the belt and the channels in the deck that provide a vacuum, limitations on the position of the tension elements internal to the belt relative to the desired vacuum pattern, breakage of the belt under load, excessive wear from V-guides used as tracking elements in a belt, delamination of facings, such as nylon fabric, on the second, deck facing surface of a belt. As referred to above, mistrack is defined as a relative difference in the cross machine direction between a predetermined target value and a value that is greater than or less than the predetermined target value. As such, during use the belt may need to be moved in the cross direction to maintain the required alignment, also referred to as the predetermined target value. Vacuum conveyors often require considerable set up to maintain belt alignment parallel to the longitudinal machine direction. Precision machining operations to minimize belt mistrack add considerable capital cost and complexity to conveyors.

It is to be appreciated that the use of angled teeth in place of the straight teeth may provide a reduction in noise levels and may align the conveyor belt to the conveyor drive and deck. Some available belts utilize multiple rows of angled teeth where each row abuts the adjacent row along the cross direction. However, utilizing a plurality of rows of angled teeth on the belt may present other difficulties. For example, multiple rows of angled teeth on either the belt or gears may not be disposed at a constant width in the cross machine direction, which may result in excessive forces acting internal to the belt. For example, having the belt fixed with a plurality of rows of angled teeth does not allow the belt to give in to or adjust to cross directional movement. In turn, cross directional repositioning of the belt to maintain proper alignment may exert cross directional forces on the belt, resulting in premature belt failure and/or excessive wear.

Thus, a need exists for a method and an apparatus for conveying absorbent articles that maintains a belt at a desired alignment in the cross machine direction while also providing relatively lower noise levels.

SUMMARY OF THE INVENTION

Aspects of the present disclosure relate to an apparatus and method for conveying absorbent articles. The apparatus may include a conveyor for conveying absorbent articles. The conveyor may include a vacuum source and a deck having a length extending in a machine direction, a width extending in a cross direction, and a channel extending in the machine direction. The deck may be fluidly connected to the vacuum source. The conveyor may also comprise a belt including a first surface, an opposing second surface, and a row of apertures extending in the machine direction. The second surface of the belt may be in facing relationship with the deck so that one or more apertures of the row of apertures are aligned with the channel. A first row of angled teeth and a second row of straight teeth may be connected with the second surface of the belt. The conveyor may also include an axle member having a first end portion, a second end portion opposite the first end portion, and a length extending in the cross direction. The axle member may be adapted to rotate about a longitudinal axle axis of rotation. A first gear member may be connected with the axle member. The first gear member may be positioned such that it is adjacent to the first end portion of the axle member. The first gear member may rotate with the axle member. The first gear member may comprise angled gear teeth positioned to mesh with the first row of angled teeth. Further, a second gear member may be connected with the axle member. The second gear member may be positioned adjacent to the second end portion of the axle member. The second gear member may rotate with the axle member. The second gear member may comprise straight gear teeth positioned to mesh with the second row of straight teeth.

In another embodiment, a method for conveying absorbent articles may comprise the steps of: providing a conveyor comprising a deck and a belt, the deck including a channel, and the belt including a first surface, a second surface opposite the first surface, and a row of apertures, wherein the second surface is in a facing relationship with the deck; drawing air through the channel with a vacuum source; placing an absorbent article on the first surface of the belt; meshing angled teeth of a first gear member with a first row of angled teeth connected with the second surface of the belt, and meshing straight teeth of a second gear member with a second row of straight teeth connected with the second surface of the belt, wherein the first gear member and the second gear member are connected with an axle member; advancing the belt in a machine direction; aligning the row of apertures with the channel by moving the belt in a cross direction; and holding the absorbent article onto the belt by drawing air through the row of apertures.

BRIEF DESCRIPTION OF THE DRAWINGS

FIG. 2 is a partially cut away plan view of the diaper pant shown in FIG. 1;

FIG. 3A is a cross-sectional view of the diaper pant of FIG. 2 taken along line 3A-3A;

FIG. 3B is a cross-sectional view of the diaper pant of FIG. 2 taken along line 3B-3B;

FIG. 11 is a bottom view of a portion of a belt in accordance with one non-limiting embodiment of the present disclosure;

DETAILED DESCRIPTION OF THE INVENTION

Figure 1:
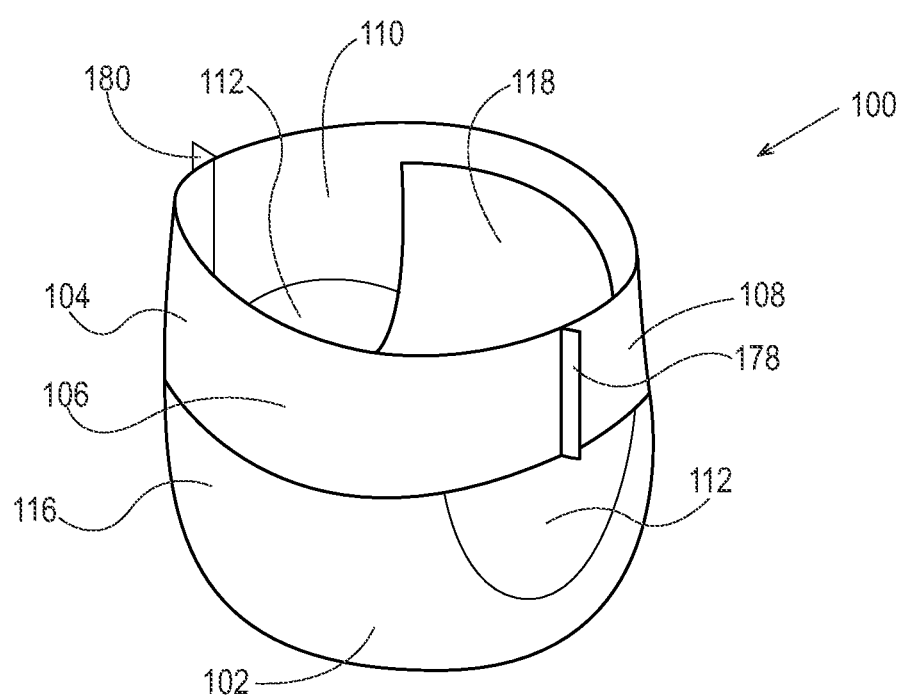
FIG. 1 is a perspective view of a diaper pant.

The following term explanations may be useful in understanding the present disclosure:

"Absorbent article" is used herein to refer to consumer products whose primary function is to absorb and retain soils and wastes. "Diaper" is used herein to refer to an absorbent article generally worn by infants and incontinent persons about the lower torso. The term "disposable" is used herein to describe absorbent articles which generally are not intended to be laundered or otherwise restored or reused as an absorbent article (e.g., they are intended to be discarded after a single use and may also be configured to be recycled, composted or otherwise disposed of in an environmentally compatible manner).

The term "pant" (also referred to as "training pant", "pre-closed diaper", "diaper pant", "pant diaper", and "pull-on diaper") refers herein to disposable absorbent articles having a continuous perimeter waist opening and continuous perimeter leg openings designed for infant or adult wearers. A pant can be configured with a continuous or closed waist opening and at least one continuous, closed, leg opening prior to the article being applied to the wearer.

The term "machine direction" (MD) is used herein to refer to the direction of material flow through a process. In addition, relative placement and movement of material may be described as flowing in the machine direction through a process from upstream in the process to downstream in the process.

The term "cross direction" (CD) is used herein to refer to a direction that is generally perpendicular to the machine direction.

The term "straight tooth" is used herein to refer to a tooth having a longitudinal tooth axis that is perpendicular to the machine direction MD. The term "angled tooth" is used here to refer to a tooth having a longitudinal axis that is not perpendicular to the machine direction MD. Any tooth that does not fit the definition of a straight tooth will be considered an angled tooth.

The present disclosure relates to a method and apparatus for conveying absorbent articles. More particularly, the apparatus herein is directed to a vacuum conveyor for transporting and/or manipulating absorbent articles. As discussed in more detail below, the vacuum conveyor may include a continuous belt and a deck. The deck may include one or more apertures or channels fluidly connected with a vacuum source. In turn, the belt may have one or more apertures aligned with the one or more channels when the belt is disposed on the deck. As such, the vacuum source creates suction across the channels in the deck and apertures in the belt. The belt is driven by a transmission mechanism having a first gear member and a second gear member. More particularly, the first gear member has teeth angled teeth, which may be helically oriented, that mesh with a first row of angled teeth on the belt. In addition, the second gear member has straight teeth that mesh with a second row of straight teeth on the belt. In use, the gear members rotate and engage the gear teeth on the belt to advance the belt in a machine direction. In addition, the engagement of the angled teeth helps maintain the desired alignment between the apertures in the belt and the channels in the deck. The angled teeth also provide relatively lower noise levels. Further, the engagement of the straight teeth allow the belt to move in the cross direction to maintain desired alignment.

It is to be appreciated that various arrangements and configurations of the apparatus herein may be used to convey and manipulate various types of articles. For example, as discussed in more detail below, the apparatus according to the present disclosure may be utilized to transport and/or to aid in the production of various components of absorbent articles, such as diapers. To help provide additional context to the subsequent discussion of the process embodiments, the following provides a general description of absorbent articles in the form of diapers that include components including the elastomeric laminates that may be produced with the methods and apparatuses disclosed herein.

FIGS. 1 and 2 show an example of a diaper pant 100 that may be transported or conveyed with the apparatuses and methods disclosed herein. In particular, FIG. 1 shows a perspective view of a diaper pant 100 in a pre-fastened configuration, and FIG. 2 shows a plan view of the diaper pant 100 with the portion of the diaper that faces away from a wearer oriented towards the viewer. The diaper pant 100 shown in FIGS. 1 and 2 includes a chassis 102 and a ring-like elastic belt 104. As discussed below in more detail, a first elastic belt 106 and a second elastic belt 108 are connected together to form the ring-like elastic belt 104.

With continued reference to FIG. 2, the chassis 102 includes a first waist region 116, a second waist region 118, and a crotch region 119 disposed intermediate the first and second waist regions. The first waist region 116 may be configured as a front waist region, and the second waist region 118 may be configured as back waist region. In some embodiments, the length of each of the front waist region, back waist region, and crotch region 120 may be ⅓ of the length of the absorbent article 100. The diaper 100 may also include a laterally extending front waist edge 121 in the front waist region 116 and a longitudinally opposing and laterally extending back waist edge 122 in the back waist region 118. To provide a frame of reference for the present discussion, the diaper 100 and chassis 102 of FIG. 2 is shown with a longitudinal axis 124 and a lateral axis 126. In some embodiments, the longitudinal axis 124 may extend through the front waist edge 121 and through the back waist edge 122. And the lateral axis 126 may extend through a first longitudinal or right side edge 128 and through a midpoint of a second longitudinal or left side edge 130 of the chassis 102.

As shown in FIGS. 1 and 2, the diaper pant 100 may include an inner, body facing surface 132, and an outer, garment facing surface 134. The chassis 102 may include a backsheet 136 and a topsheet 138. The chassis 102 may also include an absorbent assembly 140 including an absorbent core 142 that may be disposed between a portion of the topsheet 138 and the backsheet 136. As discussed in more detail below, the diaper 100 may also include other features, such as leg elastics and/or leg cuffs to enhance the fit around the legs of the wearer.

As shown in FIG. 2, the periphery of the chassis 102 may be defined by the first longitudinal side edge 128, a second longitudinal side edge 130; a first laterally extending end edge 144 disposed in the first waist region 116; and a second laterally extending end edge 146 disposed in the second waist region 118. Both side edges 128 and 130 extend longitudinally between the first end edge 144 and the second end edge 146. As shown in FIG. 2, the laterally extending end edges 144 and 146 are located longitudinally inward from the laterally extending front waist edge 121 in the front waist region 116 and the laterally extending back waist edge 122 in the back waist region 118. When the diaper pant 100 is worn on the lower torso of a wearer, the front waist edge 121 and the back waist edge 122 of the chassis 102 may encircle a portion of the waist of the wearer. At the same time, the chassis side edges 128 and 130 may encircle at least a portion of the legs of the wearer. And the crotch region 120 may be generally positioned between the legs of the wearer with the absorbent core 142 extending from the front waist region 116 through the crotch region 120 to the back waist region 118.

It is also to be appreciated that a portion or the whole of the diaper 100 may also be made laterally extensible. The additional extensibility may help allow the diaper 100 to conform to the body of a wearer during movement by the wearer. The additional extensibility may also help, for example, allow the user of the diaper 100 including a chassis 102 having a particular size before extension to extend the front waist region 116, the back waist region 118, or both waist regions of the diaper 100 and/or chassis 102 to provide additional body coverage for wearers of differing size, i.e., to tailor the diaper to an individual wearer. Such extension of the waist region or regions may give the absorbent article a generally hourglass shape, so long as the crotch region is extended to a relatively lesser degree than the waist region or regions, and may impart a tailored appearance to the article when it is worn.

As previously mentioned, the diaper pant 100 may include a backsheet 136. The backsheet 136 may also define the outer surface 134 of the chassis 102. The backsheet 136 may be impervious to fluids (e.g., menses, urine, and/or runny feces) and may be manufactured from a thin plastic film, although other flexible liquid impervious materials may also be used. The backsheet 136 may prevent the exudates absorbed and contained in the absorbent core from wetting articles which contact the diaper 100, such as bedsheets, pajamas, and undergarments. The backsheet 136 may also comprise a woven or nonwoven material, polymeric films such as thermoplastic films of polyethylene or polypropylene, and/or a multi-layer or composite materials comprising a film and a nonwoven material (e.g., having an inner film layer and an outer nonwoven layer). The backsheet may also comprise an elastomeric film. An example backsheet 136 may be a polyethylene film having a thickness of from about 0.012 mm (0.5 mils) to about 0.051 mm (2.0 mils). Exemplary polyethylene films are manufactured by Clopay Corporation of Cincinnati, Ohio, under the designation BR-120 and BR-121 and by Tredegar Film Products of Terre Haute, Ind., under the designation XP-39385. The backsheet 136 may also be embossed and/or matte-finished to provide a more clothlike appearance. Further, the backsheet 136 may permit vapors to escape from the absorbent core (i.e., the backsheet is breathable) while still preventing exudates from passing through the backsheet 136. The size of the backsheet 136 may be dictated by the size of the absorbent core 142 and/or particular configuration or size of the diaper 100.

Also described above, the diaper pant 100 may include a topsheet 138. The topsheet 138 may also define all or part of the inner surface 132 of the chassis 102. The topsheet 138 may be compliant, soft feeling, and non-irritating to the wearer's skin. It may be elastically stretchable in one or two directions. Further, the topsheet 138 may be liquid pervious, permitting liquids (e.g., menses, urine, and/or runny feces) to penetrate through its thickness. A topsheet 138 may be manufactured from a wide range of materials such as woven and nonwoven materials; apertured or hydroformed thermoplastic films; apertured nonwovens, porous foams; reticulated foams; reticulated thermoplastic films; and thermoplastic scrims. Woven and nonwoven materials may comprise natural fibers such as wood or cotton fibers; synthetic fibers such as polyester, polypropylene, or polyethylene fibers; or combinations thereof. If the topsheet 138 includes fibers, the fibers may be spunbond, carded, wet-laid, meltblown, hydroentangled, or otherwise processed as is known in the art.

Topsheets 138 may be selected from high loft nonwoven topsheets, apertured film topsheets and apertured nonwoven topsheets. Apertured film topsheets may be pervious to bodily exudates, yet substantially non-absorbent, and have a reduced tendency to allow fluids to pass back through and rewet the wearer's skin. Exemplary apertured films may include those described in U.S. Pat. Nos. 5,628,097; 5,916,661; 6,545,197; and 6,107,539.

As mentioned above, the diaper pant 100 may also include an absorbent assembly 140 that is joined to the chassis 102. As shown in FIG. 2, the absorbent assembly 140 may have a laterally extending front edge 148 in the front waist region 116 and may have a longitudinally opposing and laterally extending back edge 150 in the back waist region 118. The absorbent assembly may have a longitudinally extending right side edge 152 and may have a laterally opposing and longitudinally extending left side edge 154, both absorbent assembly side edges 152 and 154 may extend longitudinally between the front edge 148 and the back edge 150. The absorbent assembly 140 may additionally include one or more absorbent cores 142 or absorbent core layers. The absorbent core 142 may be at least partially disposed between the topsheet 138 and the backsheet 136 and may be formed in various sizes and shapes that are compatible with the diaper. Exemplary absorbent structures for use as the absorbent core of the present disclosure are described in U.S. Pat. Nos. 4,610,678; 4,673,402; 4,888,231; and 4,834,735.

Some absorbent core embodiments may comprise fluid storage cores that contain reduced amounts of cellulosic airfelt material. For instance, such cores may comprise less than about 40%, 30%, 20%, 10%, 5%, or even 1% of cellulosic airfelt material. Such a core may comprises primarily absorbent gelling material in amounts of at least about 60%, 70%, 80%, 85%, 90%, 95%, or even about 100%, where the remainder of the core comprises a microfiber glue (if applicable). Such cores, microfiber glues, and absorbent gelling materials are described in U.S. Pat. Nos. 5,599,335; 5,562,646; 5,669,894; and 6,790,798 as well as U.S. Patent Publication Nos. 2004/0158212 and 2004/0097895.

As previously mentioned, the diaper 100 may also include elasticized leg cuffs 156. It is to be appreciated that the leg cuffs 156 can be and are sometimes also referred to as leg bands, side flaps, barrier cuffs, elastic cuffs or gasketing cuffs. The elasticized leg cuffs 156 may be configured in various ways to help reduce the leakage of body exudates in the leg regions. Example leg cuffs 156 may include those described in U.S. Pat. Nos. 3,860,003; 4,909,803; 4,695,278; 4,795,454; 4,704,115; 4,909,803; U.S. Patent Publication No. 2009/0312730A1; and U.S. Patent Publication No. 2013/0255865A1.

As mentioned above, diaper pants may be manufactured with a ring-like elastic belt 104 and provided to consumers in a configuration wherein the front waist region 116 and the back waist region 118 are connected to each other as packaged, prior to being applied to the wearer. As such, diaper pants may have a continuous perimeter waist opening 110 and continuous perimeter leg openings 112 such as shown in FIG. 1. As previously mentioned, the ring-like elastic belt 104 is defined by a first elastic belt 106 connected with a second elastic belt 108. As shown in FIG. 2, the first elastic belt 106 defines first and second opposing end regions 106a, 106b and a central region 106c, and the second elastic 108 belt defines first and second opposing end regions 108a, 108b and a central region 108c.

The central region 106c of the first elastic belt is connected with the first waist region 116 of the chassis 102, and the central region 108c of the second elastic belt 108 is connected with the second waist region 118 of the chassis 102. As shown in FIG. 1, the first end region 106a of the first elastic belt 106 is connected with the first end region 108a of the second elastic belt 108 at first side seam 178, and the second end region 106b of the first elastic belt 106 is connected with the second end region 108b of the second elastic belt 108 at second side seam 180 to define the ring-like elastic belt 104 as well as the waist opening 110 and leg openings 112.

As shown in FIGS. 2, 3A, and 3B, the first elastic belt 106 also defines an outer lateral edge 107a and an inner lateral edge 107b, and the second elastic belt 108 defines an outer lateral edge 109a and an inner lateral edge 109b. The outer lateral edges 107a, 109a may also define the front waist edge 121 and the laterally extending back waist edge 122. The first elastic belt and the second elastic belt may also each include an outer, garment facing layer 162 and an inner, wearer facing layer 164. It is to be appreciated that the first elastic belt 106 and the second elastic belt 108 may comprise the same materials and/or may have the same structure. In some embodiments, the first elastic belt 106 and the second elastic belt may comprise different materials and/or may have different structures. It should also be appreciated that the first elastic belt 106 and the second elastic belt 108 may be constructed from various materials. For example, the first and second belts may be manufactured from materials such as plastic films; apertured plastic films; woven or nonwoven webs of natural materials (e.g., wood or cotton fibers), synthetic fibers (e.g., polyolefins, polyamides, polyester, polyethylene, or polypropylene fibers) or a combination of natural and/or synthetic fibers; or coated woven or nonwoven webs. In some embodiments, the first and second elastic belts may include a nonwoven web of synthetic fibers, and may include a stretchable nonwoven. In other embodiments, the first and second elastic belts may include an inner hydrophobic, non-stretchable nonwoven material and an outer hydrophobic, non-stretchable nonwoven material.

The first and second elastic belts 106, 108 may also each include belt elastic material interposed between the outer layer 162 and the inner layer 164. The belt elastic material may include one or more elastic elements such as strands, ribbons, or panels extending along the lengths of the elastic belts. As shown in FIGS. 2, 3A, and 3B, the belt elastic material may include a plurality of elastic strands 168 that may be referred to herein as outer, waist elastics 170 and inner, waist elastics 172.

As shown in FIG. 2, the outer, waist elastics 170 extend continuously laterally between the first and second opposing end regions 106a, 106b and across the central region 106c of the first elastic belt 106 and between the first and second opposing end regions 108a, 108b and across the central region 108c of the second elastic belt 108. In some embodiments, some elastic strands 168 may be configured with discontinuities in areas. For example, as shown in FIG. 2, the inner, waist elastics 172 extend intermittently along the first and second elastic belts 106, 108. More particularly, the inner, waist elastics 172 extend along the first and second opposing end regions 106a, 106b and partially across the central region 106c of the first elastic belt 106. The inner, waist elastics 172 also extend along the first and second opposing end regions 108a, 108b and partially across the central region 108c of the second elastic belt 108. As such, the inner, waist elastics 172 do not extend across the entirety of the central regions 106c, 108c of the first and second elastic belts 106, 108. Thus, some elastic strands 168 may not extend continuously through regions of the first and second elastic belts 106, 108 where the first and second elastic belts 106, 108 overlap the absorbent assembly 140. In some embodiments, some elastic strands 168 may partially extend into regions of the first and second elastic belts 106, 108 where the first and second elastic belts 106, 108 overlap the absorbent assembly 140. In some embodiments, some elastic strands 168 may not extend into any region of the first and second elastic belts 106, 108 where the first and second elastic belts 106, 108 overlap the absorbent assembly 140. It is to be appreciated that the first and/or second elastic belts 106, 108 may be configured with various configurations of discontinuities in the outer, waist elastics 170 and/or the inner, waist elastic elastics 172.

In some embodiments, the elastic strands 168 may be disposed at a constant interval in the longitudinal direction. In other embodiments, the elastic strands 168 may be disposed at different intervals in the longitudinal direction. As discussed in more detail below, the belt elastic strands 168, in a stretched condition, may be interposed and joined between the uncontracted outer layer and the uncontracted inner layer. When the belt elastic material is relaxed, the belt elastic material returns to an unstretched condition and contracts the outer layer and the inner layer. The belt elastic material may provide a desired variation of contraction force in the area of the ring-like elastic belt. It is to be appreciated that the chassis 102 and elastic belts 106, 108 may be configured in different ways other than as depicted in FIG. 2.

As previously mentioned, the apparatuses and methods according to the present disclosure may be utilized to convey and/or advance discrete absorbent articles 100 and/or various components of absorbent articles 100, such as for example, chassis 102, elastic belts 106, 108, and/or leg cuffs 156. Although the following methods may be provided in the context of the diaper 100 shown in FIGS. 1 and 2, it is to be appreciated that the methods and apparatuses herein may be used with various process configurations and/or absorbent articles, such as for example, disclosed in U.S. Pat. No. 7,569,039; U.S. Patent Publication Nos. US2005/0107764A1, US2012/0061016A1, and US2012/0061015A1; 2013/0255861A1; 2013/0255862A1; 2013/0255863A1; 2013/0255864A1; and 2013/0255865A1, all of which are incorporated by reference herein.

Figure 4:
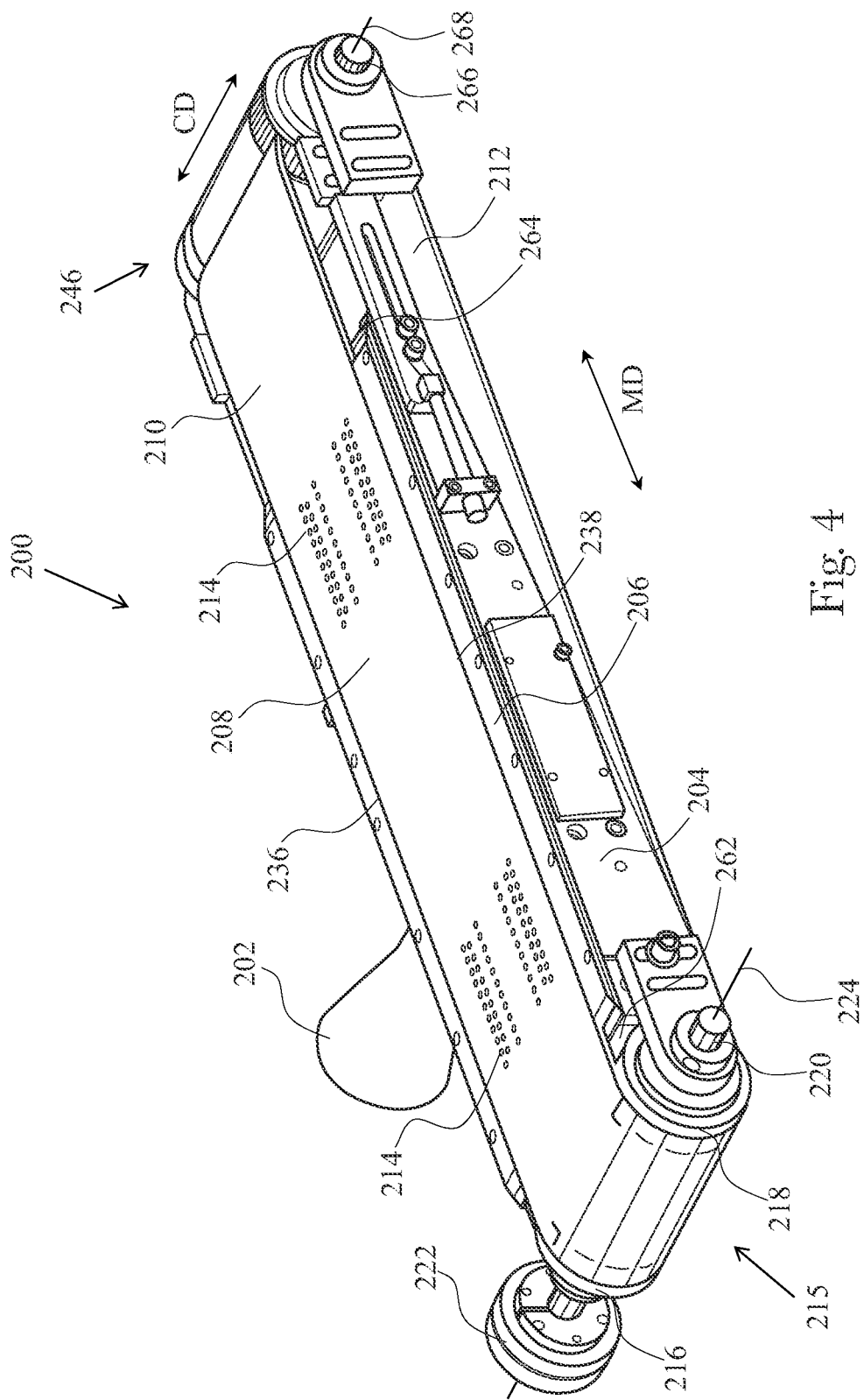
FIG. 4 is a perspective view of a conveyor in accordance with one non-limiting embodiment of the present disclosure.
Figure 5:
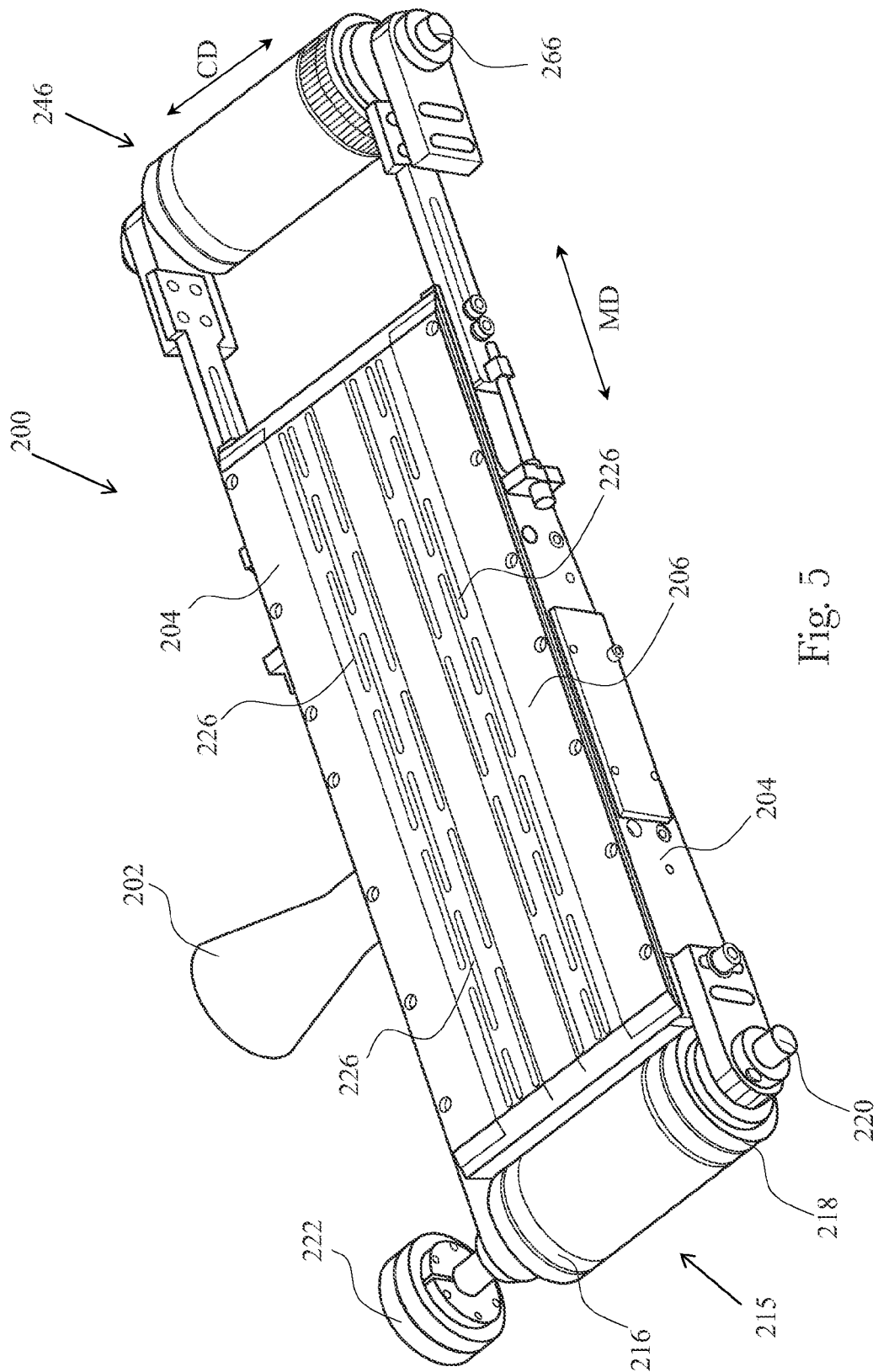
FIG. 5 is a perspective view of a deck in combination with a transmission mechanism and a guide mechanism in accordance with one non-limiting embodiment of the present disclosure.

FIG. 4 shows an embodiment of the vacuum conveyor 200 that may be used to transport and/or manipulate an absorbent article 100. As shown, the vacuum conveyor 200 may include a vacuum source 202. The vacuum source 202 may be in fluid connection with a deck 204. Thus, the vacuum source 202 may be configured to pull air away from the deck 204. The deck 204 has a first deck end 262 and a second deck end 264, opposite the first deck end 262, defining a length therebetween that extends in the machine direction MD. Further, the deck 204 has a width extending in the cross direction CD. The deck 204 may comprise one or more channels, as shown in FIG. 5, extending in the machine direction MD and located on the deck surface 206 of the deck 204. With continued reference to FIG. 4, the belt 208 may be adjacent the deck surface 206. The belt 208 has a length extending in the machine direction MD and a width extending in the cross direction CD. Further, the belt 208 may include a first surface 210, a second surface 212 opposite the first surface 210, a first edge 236, and a second edge 238 opposite the first edge 236. The second surface 212 of the belt 208 may be in facing relationship with the deck surface 206 and the first surface 210 may be exposed to one or more absorbent articles. The belt 208 may also include one or more apertures 214 disposed between the first edge 236 and the second edge 238. Further, each aperture 214 defined by the belt 208 may be aligned with at least one channel on the deck 204. Thus, air can be drawn through the apertures 214 and subsequently through the channels 226 into the deck 204 and out to the vacuum source 202.

The belt 208 may further comprise a first row of teeth and a second row of teeth, discussed in more detail below, disposed on the second surface 212 of the belt 208. In one embodiment, a first row of teeth and a second row of teeth attached to the belt 208 may be used by the transmission mechanism 215 to move the belt. The transmission mechanism 215 may be adjacent to the first deck end 262 and configured to engage and drive the belt. More specifically, the first row of teeth may engage a first gear member 216 and the second row of teeth may engage a second gear member 218. The first gear member 216 and the second gear member 218 may be positioned on an axle member 220 that is driven by a drive mechanism 222, such as a rotary motor. Thus, as the axle member 220 rotates, the first gear member 216 and the second gear member 218 rotate about the longitudinal axle axis 224 of the axle member 220. The rotation of the first gear member 216 and the second gear member 218 may move the belt 208 across the deck surface 206 in the machine direction MD.

As shown in FIG. 4, a guide mechanism 246 may be positioned opposite the transmission mechanism 215 and adjacent to the second deck end 264. The guide mechanism 246 may be configured to guide the belt 208 during operation of the conveyor 200. For example, for a conveyor comprising a continuous-loop belt, the belt would be required to be directed back over the deck surface during operation. The guide mechanism 246 may comprise a shaft 266 that may rotate about a longitudinal shaft axis 268. The shaft 266 may be adapted to support the belt 208. In an alternative embodiment, not shown, it is believed that the drive mechanism 222 may also operatively engage the shaft 266 such that the drive mechanism 222 causes the shaft 266 to rotate about the longitudinal shaft axis 268. The rotation of the shaft 266 may move the belt 208 in the machine direction MD.

Figure 6:
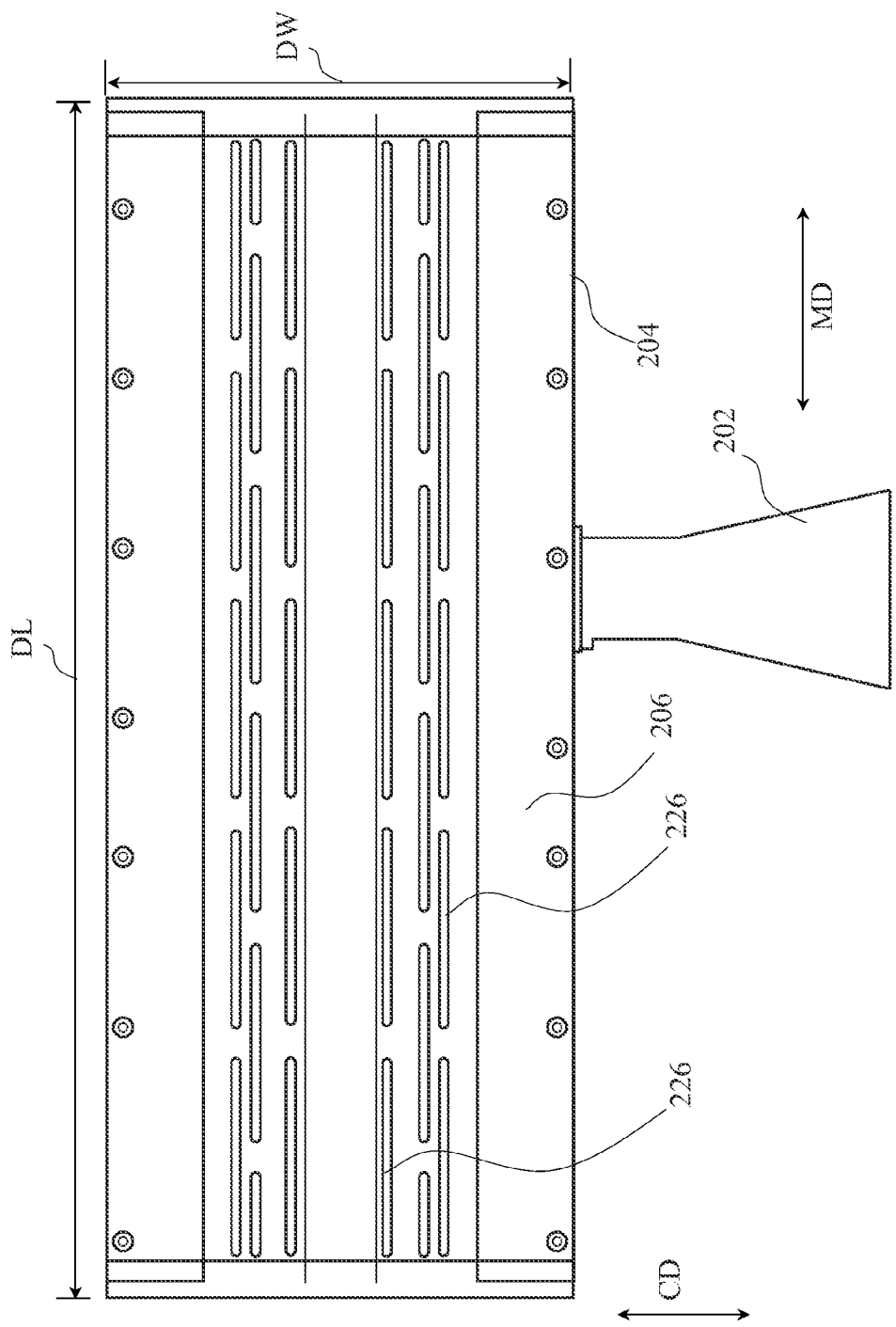
FIG. 6 a top view of a deck in fluid connection with a vacuum source in accordance with one non-limiting embodiment of the present disclosure.

Referring to FIGS. 5 and 6, as stated above, the vacuum source 202 may be connected to the deck 204 such that air can be drawn from the deck 204 to the vacuum source 202.

The deck 204 has a deck length DL extending in the machine direction MD and a deck width DW extending in the cross direction CD. In one embodiment, the deck length DL should be sufficient to hold at least one absorbent article. The deck length DL may be from about 150 mm to about 2000 mm and/or from about 300 mm to about 3000 mm. Similarly, the deck width DW should be long enough to support the width of the belt 208. For example, in one embodiment, the deck width DW may be from about 150 mm to about 800 mm. The deck 204 may comprise a deck surface 206. The deck surface 206 may define one or more channels 226. The channels 226 may extend through the deck surface 206 so that each channel 226 is in fluid connection with the vacuum source 202. Each channel 226 may have a size and a shape. The size and shape of each channel 226 may be different than or the same as the size and shape of another channel 226. However, the size and shape of the channel 226 should be sufficient to provide the desired suction either alone or in combination with the belt 208. In one example embodiment, as shown in FIG. 6, the channels 226 may be an elongated, oval shape. Further, the channel 226 may be positioned on the deck surface 206 such that the apertures 214 in the belt 208 undergo a substantially constant vacuum when disposed on the deck surface 206. The deck 204 may be made from any material that has sufficient strength to withstand the load of the belt and articles to be conveyed and sufficient structural rigidity to withstand one more channels 226 that may extend through the deck surface 206. For example, the deck 204 may be made from steel, aluminum, ceramic, phenolic plate, and/or polymer elements, including but not limited to UHMW polymer, Teflon, phenolic polymer, and/or delrin. The deck surface 206 may also be anodized, electroplated, vapor deposition coated, polymer coated, or ceramic coated to reduce the coefficient of friction and to reduce wear.

Figure 7:
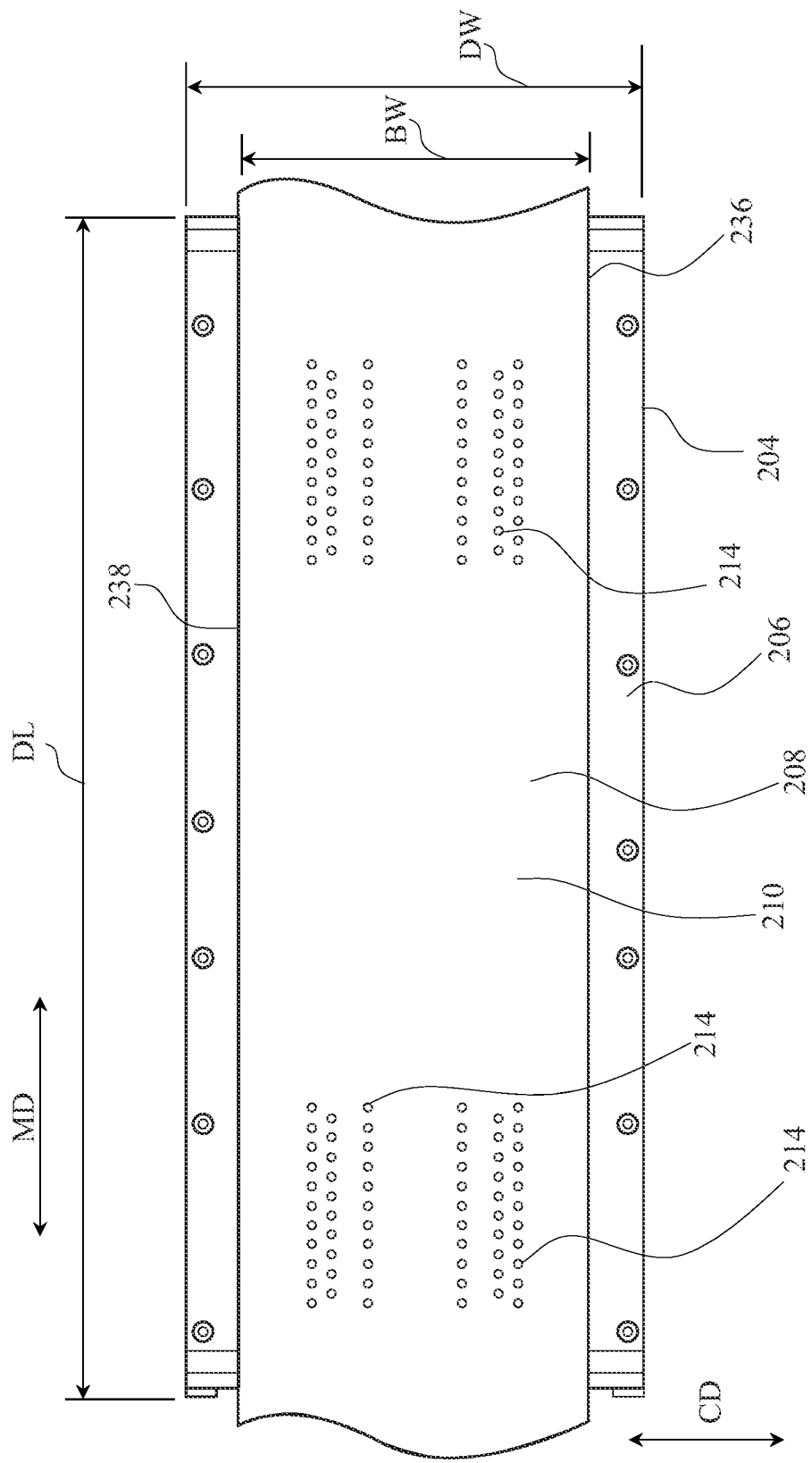
FIG. 7 is a top view of a portion of a belt disposed on a deck in accordance with one non-limiting embodiment of the present disclosure.

As shown in FIG. 7, the belt 208 may extend across at least a portion of the deck surface 206. More specifically, the belt 208 may be positioned on the deck surface 206 such that the entire belt width BW is supported by the deck surface 206. Stated another way, in one embodiment, the belt width BW may be less than or equal to the deck width DW. The belt 208 may comprise a first edge 236 and a second edge 238 opposite the first edge 236. Further, the belt may comprise one or more apertures 214 located within the first edge 236 and the second edge 238. In one embodiment, the one or more apertures 214 may be positioned in rows. Further, the belt 208 may be positioned on the deck surface 206 such that the rows of apertures 214 are in fluid connection with the one or more channels 226 on the deck surface 206. If the belt 208 remains in proper alignment such that the apertures 214 are in fluid connection with the channels 226, the apertures 214 may be designed to have a smaller cross section. Stated another way, if a manufacturer knew that the apertures 214 on the belt 208 would not become misaligned with the channels 226, the manufacturer could design the apertures 214 to have a smaller cross section and/or a cross section that corresponds to the cross section of the channel and, thus, require less energy to obtain a greater suction.

Alternatively, if it was known that the apertures 214 on the belt 208 could become misaligned, also referred to as mistrack, during processing, the apertures 214 would have to be designed to have a larger cross section so that at least some portion of the aperture may remain in fluid connectivity with the channel 226 when the belt was misaligned. Having to design a larger aperture 214 may result in higher energy to obtain and/or maintain the desired suction on the article. The vacuum source 202 would be required to pull more air through the aperture 214 to maintain the desired suction over the absorbent article. Thus, reducing the mistrack of belt 208 allows a smaller CD dimension of channels 226 for a given CD width of apertures 214 and a smaller CD dimension of apertures 214 in the belt 208, which may result in increased strength of the belt 208. Reducing mistrack may also allow process benefits such as increasing the vacuum force on absorbent article to be increased and/or allowing for a broader cross sectional design of apertures 214 and/or tolerating closer spacing of apertures 14 for a given construction of belt 208. Accordingly, it is important that the belt 208 maintain its orientation in the CD such that the one or more apertures 214 remain substantially aligned with the one or more channels 226.

The one or more apertures 214 may be placed in any number of configurations on the belt 208. The one or more apertures 214 may be sized to generate the desired suction on the article given the configuration of the channels 226 and the capability of the vacuum source 202 to draw in air. Each aperture 214 may be shaped to maximize the ability to control the absorbent article. For example, in one embodiment, as shown in FIG. 7, the apertures 214 may be circular in shape. In an alternate embodiment, not shown, the apertures may be elongated ovals, to maximize the cross section area of apertures 214 in fluid communication with the disposable absorbent article for a given CD width of channels 226. Further to the above, placement of the one or more apertures 214 should be designed in view of the placement of the channels 226 on the deck surface 206 and/or size of the article to be acted on. The apertures 214 should be placed on the belt 208 such that when the belt 208 overlays the deck surface 206 the one or more apertures 214 are in fluid contact with the channels 226. Fluid contact means that the vacuum source may pull air through the aperture 214 and the adjacent channel 226 and into the deck 204.

Further to the above, the placement of the one or more apertures 214 may result in the belt 208 having reduced strength. During high-speed manufacturing, the belt 208 may undergo stresses in both the machine direction MD and the cross machine direction CD. Removing material from the belt 208 to create the one or more apertures 214 may decrease the shear strength of the belt 208. However, placement of the apertures 214, material selection for the belt 208, belt fabrication, and how the belt 208 is driven during manufacture may help maintain the structural integrity of the belt 208 during use. For example, in one embodiment, the belt may be manufactured from one or more layers of woven fabrics, such as polyester. In another example embodiment, the belt may be fabricated from polyurethane and include reinforcement cords, also referred to as tension elements, which may be made of KEVLAR, steel, or carbon fiber, that extend in the machine direction MD. In yet another embodiment, the belt 208 may be fabricate d such that the belt contains one or more rows of teeth that aid in alignment of the belt with respect to the deck.

Figure 8:
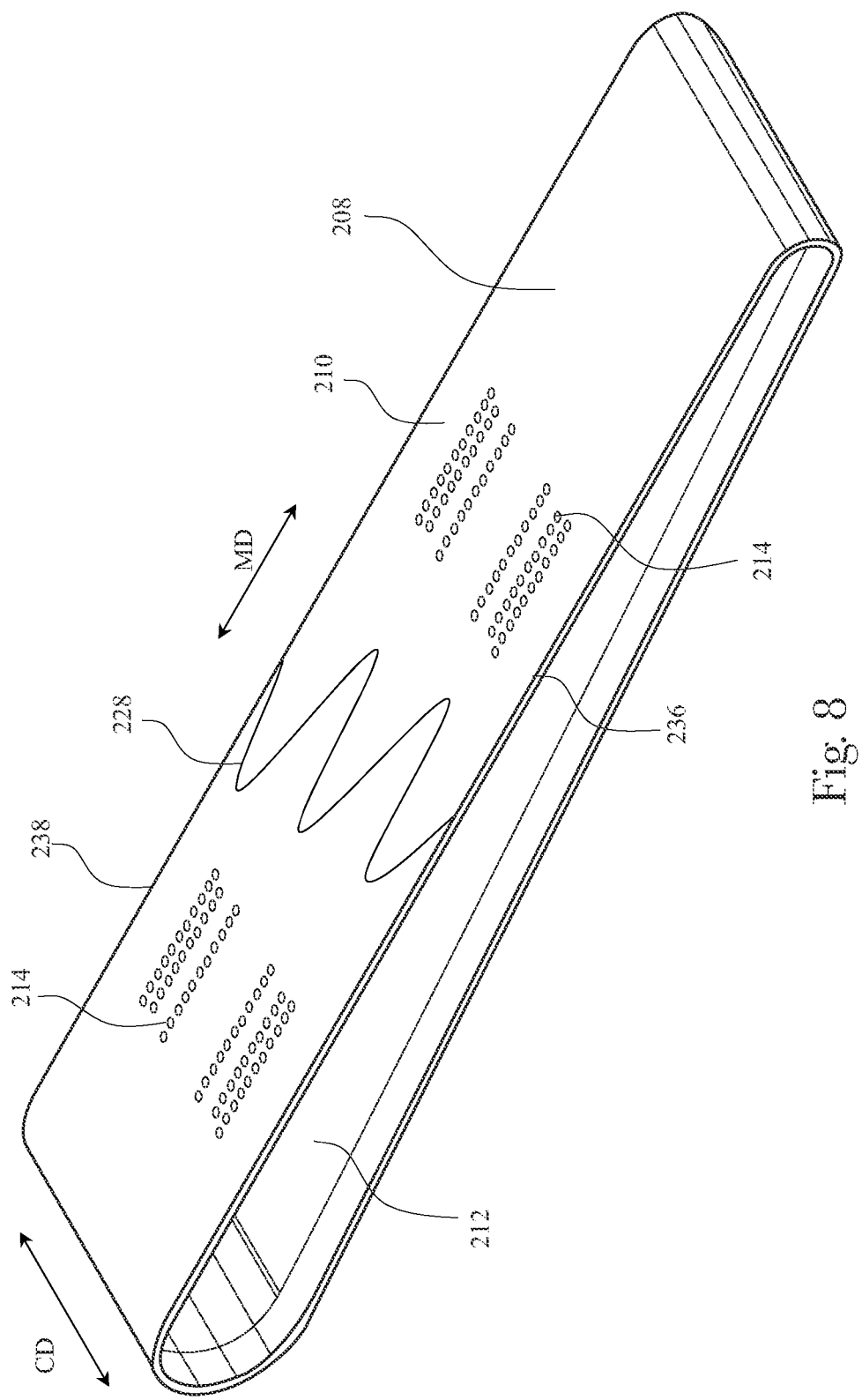
FIG. 8 is a perspective view of a continuous belt in accordance with one non-limiting embodiment of the present disclosure.

A belt 208, as shown in FIG. 8, may be configured such that it forms a continuous loop. To form the continuous loop, the belt 208 may comprise a seam 228. The seam 228 may be the location at which the two ends of the belt are joined. The seam 228 should be strong enough to withstand the stresses exerted on the belt 208 during the manufacturing process. Due to the configuration of the belt as a continuous loop, the second surface 212 of the belt may maintain engagement with the transmission mechanism 215 and the guide mechanism 246 during the manufacture of the absorbent articles. Thus, the second surface 212 of the belt 208 may be connected to one or more rows of teeth to interact with the transmission mechanism 215 and the guide mechanism 246.

Figure 9:
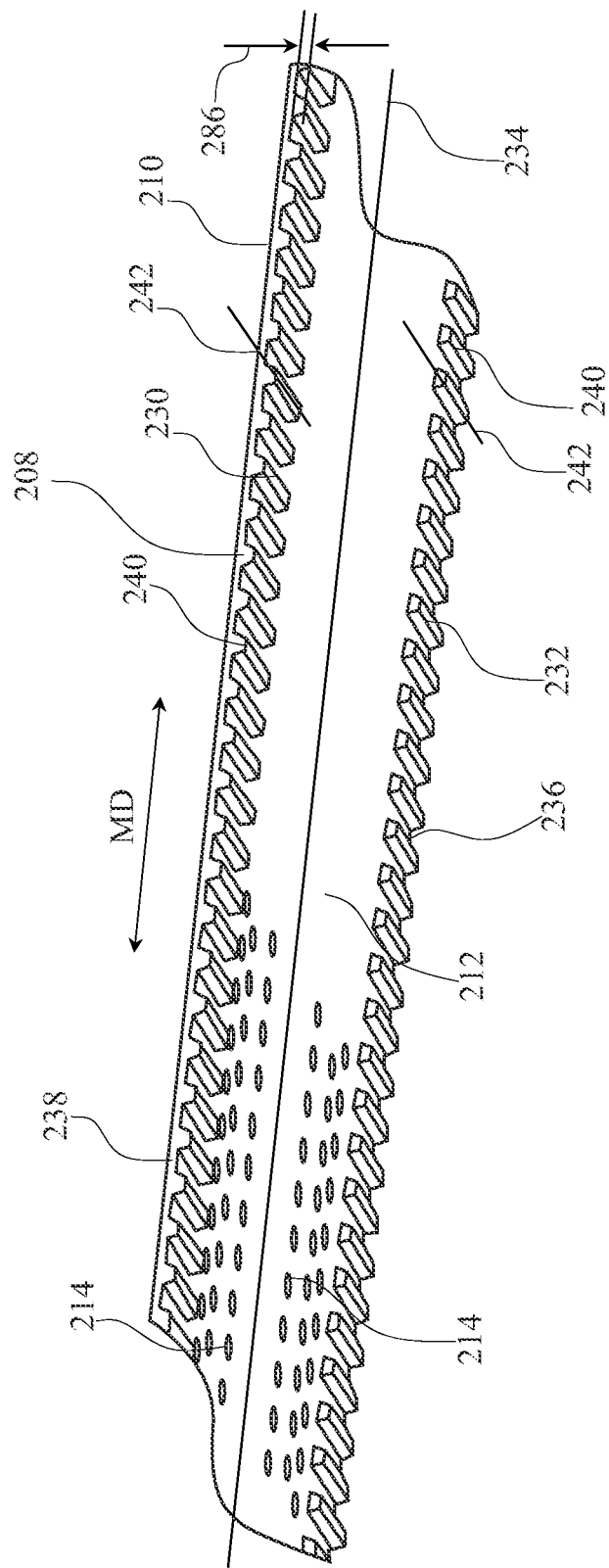
FIG. 9 is a perspective view of a portion of the second side of a belt in accordance with one non-limiting embodiment of the present disclosure.
Figure 10C:
FIG. 10C is a schematic representation of the shape of a tooth in accordance with one non-limiting embodiment of the present disclosure.
Figure 10F:
FIG. 10F is a schematic representation of the shape of a tooth in accordance with one non-limiting embodiment of the present disclosure.
Figure 10B:
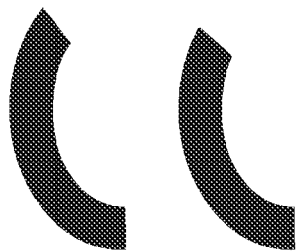
FIG. 10B is a schematic representation of the shape of a tooth in accordance with one non-limiting embodiment of the present disclosure.
Figure 10E:
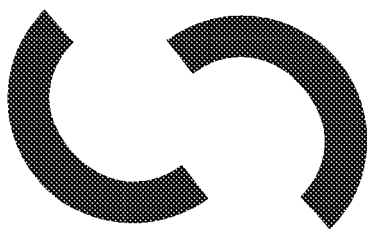
FIG. 10E is a schematic representation of the shape of a tooth in accordance with one non-limiting embodiment of the present disclosure.
Figure 10A:
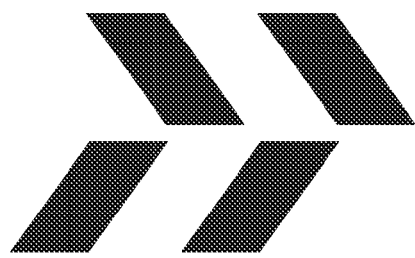
FIG. 10A is a schematic representation of the shape of a tooth in accordance with one non-limiting embodiment of the present disclosure.
Figure 10D:
FIG. 10D is a schematic representation of the shape of a tooth in accordance with one non-limiting embodiment of the present disclosure.

Referring to FIG. 9, the second surface 212 of the belt 208 may comprise a central longitudinal axis 234 extending in the machine direction MD and substantially parallel to the machine direction MD. The central longitudinal axis 234 is intermediate the first edge 236 of the belt 208 and the second edge 238 of the belt 208. The belt 208 may also comprise one or more rows of teeth 230, 232. In one example embodiment, a first row of teeth 230 and a second row of teeth 232 may be connected with the second surface 212 of the belt 208. The first row of teeth 230 and the second row of teeth 232 may extend in the machine direction MD and may be positioned about the central longitudinal axis 234 of the belt 208. More specifically, the first row of teeth 230 may be disposed along the first edge 236 of the belt 208 and the second row of teeth 232 may be disposed along the second edge 238 of the belt 208.

Each row of teeth 230, 232 may be configured to interact with a transmission mechanism 215 to drive the belt in the machine direction MD, which will be described in more detail below. Still referring to FIG. 9, belt 208 may be manufactured with two or more rows of teeth 230, 232. Each tooth 240 within a row of teeth may comprise a longitudinal tooth axis 242 that may be oriented perpendicular to or at an angle to the machine direction MD. A tooth having a longitudinal tooth axis 242 that is perpendicular to the machine direction MD of the belt 208 is referred to as a straight tooth. Further, a row of teeth comprising teeth that each have a longitudinal tooth axis 242 that is perpendicular to the machine direction MD of the belt 208 is referred to as a straight row of teeth or a row of teeth comprising straight teeth.

A belt 208 comprising only rows of teeth including straight teeth may result in several problems, such as those previously stated. A straight tooth orientation allows the belt 208 to move in the cross direction CD during the manufacturing process. Stated another way, the straight rows of teeth 230, 232 allow the belt 208 to move freely in the cross direction because the teeth provide little to no force in the cross direction CD. Thus, the apertures 214 in the belt 208 may easily become misaligned with the one or more channels 226 present in the deck surface 206. Misalignment of the apertures 214 with the channels 226 may result in several problems such the aforementioned and also including loss of control over the articles and/or article defects. Further, straight teeth result in very high noise levels. For example, a conveyor 200, as shown in FIG. 4, comprising a belt 208 having one or more rows of teeth including straight teeth, as shown in FIG. 9, often require a noise insulating guard to substantially surround the conveyor to protect workers from high noise levels. However, even with the insulating guard, workers may still be required to wear hearing protection due to high noise levels.

To solve the aforementioned problems, teeth having an angled and/or curved profile, as shown in FIGS. 10A-10F, may be connected to the belt 208. The angled and/or curved profile of the teeth may produce a force parallel to the cross direction CD on the belt 208. This force would restrict the belts 208 movement in the cross direction CD, which may result in maintaining alignment of the apertures 214 with the channels 226 during high speed manufacturing. Having at least one of the first row of teeth 230 and the second row of teeth 232 comprise an angled tooth may result in the belt 208 maintaining alignment with the deck 204 such that during processing the belt 208 maintains the support of the deck 204. Further, a belt 208 comprising one or more angled teeth may result in the apertures 214, defined by the surface of the belt 208, maintaining alignment with the channels 226 in the surface of the deck 204. Further still, the one or more apertures 214 may be placed such that the apertures 214 do not interfere with the tension elements, which protect the strength of the belt 208, because the angled teeth maintain the alignment of the apertures 214 with the channels 226. Finally, having a first row of teeth 230 and a second row of teeth 232 attached to the belt 208 may also result in reduced wear from a belt driven solely by frictional forces. Belts driven by devices such as V-guides are susceptible to excessive and frequent wear due to the constant fictional forces acting on the belt. These frictional forces may also result in delamination of the belt facings, such as coatings used on the surface of the belt. However, these frictional forces may be reduced by using one or more rows of teeth 230, 232 to advance the belt in the machine direction.

In one example embodiment, the belt 208 may comprise a second surface 212 including a first row of teeth 230 and a second row of teeth 232. The first row of teeth 230 and the second row of teeth 232 may include teeth that are angled. More specifically, each angled tooth comprises a longitudinal tooth axis 242 that defines an angle with respect to the machine direction MD of the belt 208. Further, each angled tooth produces a cross direction force that restricts the movement of the belt 208 in the cross direction. In one embodiment, the longitudinal tooth axis 242 may be at an angle of about 5 degree to about 85 and/or from about 15 degrees to about 75 degrees and/or about 20 degrees to about 65 degrees from the machine direction and the central longitudinal axis 234 of the belt 208, which is parallel to the machine direction MD. The angled teeth provide a positive force +F and a negative force −F substantially parallel to the cross direction CD on the belt 208 such that the movement of the belt 208 in the cross direction is limited. Stated another way, the angled teeth restrict movement in the cross direction CD so that the one or more apertures 214 on the belt 208 may maintain alignment with the one or more channels 226 on the deck surface 206 during operation.

It is to be appreciated that the first row of straight teeth and the second row of teeth may have any number of profiles, such as those shown in FIG. 10A-10F, that restrict the cross directional movement of the belt. Further, the longitudinal tooth axis 242 may be taken as an imaginary line drawn parallel to the longest dimension of the tooth.

In addition, it has been found that the use of angled teeth provide a significant reduction in noise level. Thus, a belt 208 comprising a first row of angled teeth and a second row of angled teeth as compared to a belt 208 comprising a first row of straight teeth and a second row of straight teeth, the belt having two rows of angled teeth resulted in at least about a six dBA noise reduction.

However, depending on the type of operation to be performed and/or the type of article on which the vacuum acts and/or the properties of the belt material, having angled teeth on both the first edge 236 and the second edge 238 may result in excessive force acting on the belt 208. During the manufacturing process, the belt 208 may undergo cross directional forces as a result of, for example, the weight of the article and/or the compression or extension of the belt material due to the external environment. Thus, having the belt 208 fixed with an angled tooth at both edges may not allow the belt 208 to give in to or adjust to these cross directional forces. This inability to adjust to cross directional forces may result in premature belt failure caused by, for example, tearing of the belt. Accordingly, a need exists to allow some, controlled cross directional movement of the belt 208.

In view of the aforementioned problems, it has been found that a belt 208 comprising a first row teeth 230 having angled teeth and a second row of teeth having straight teeth, as shown in FIG. 11, allows the belt 208 sufficient movement in the cross direction CD. This cross directional movement may alleviate the cross directional forces that act on the belt 208 resulting in improved belt life and increased productivity. In addition, the angled row of teeth provides sufficient control over the CD position of the belt such that manufacturers are able to control the CD position of the belt at high manufacturing speeds. Further, this configuration results in a significant reduction in the noise level during manufacture. It is to be appreciated that any tooth profile that restricts cross directional movement of the belt 208 may be used as an angled tooth, such as those shown in FIG. 10A-10F.

Figure 12:
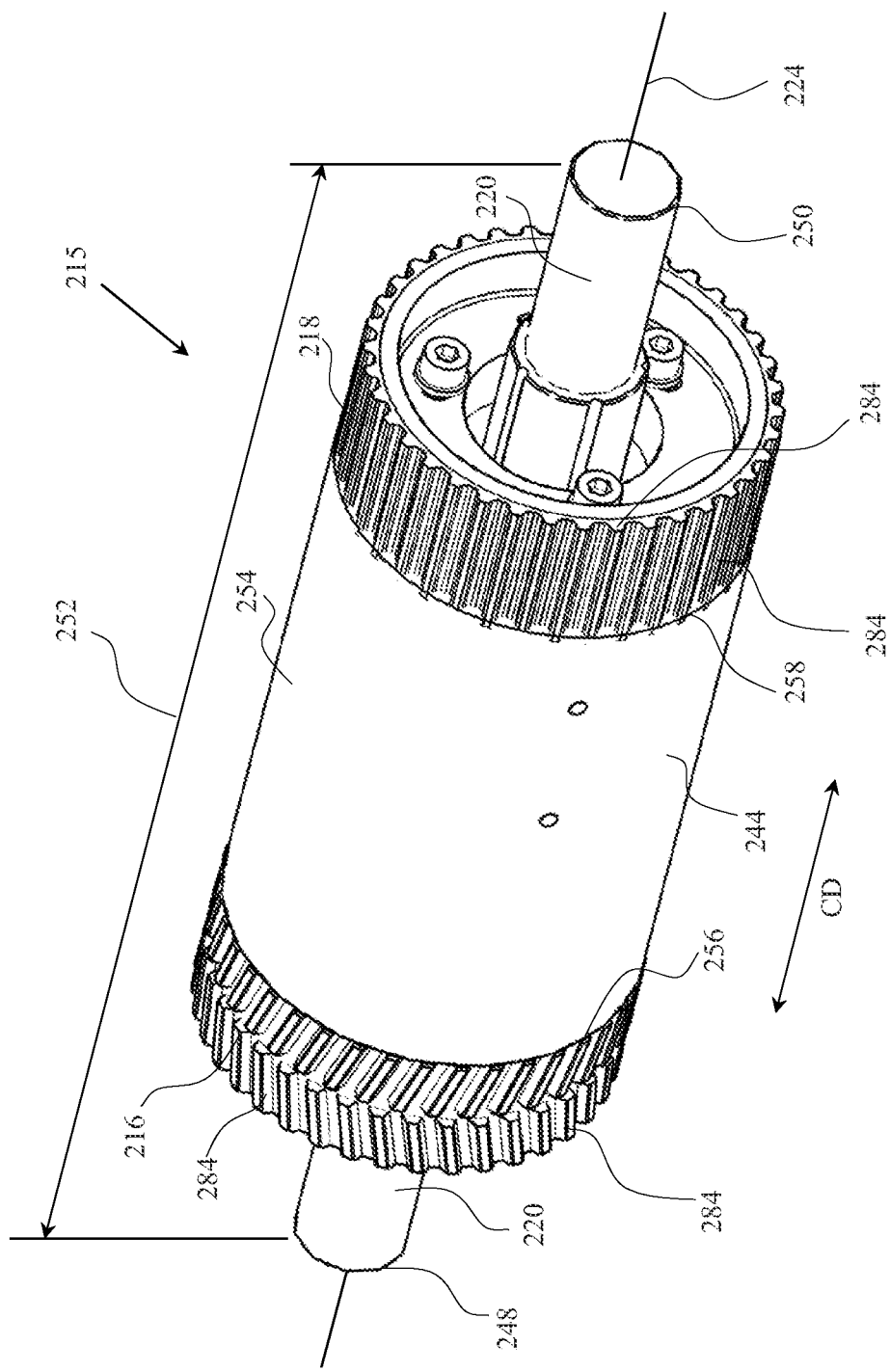
FIG. 12 is a perspective view of a transmission mechanism in accordance with one non-limiting embodiment of the present disclosure.

As previously disclosed, the belt 208 may be driven in the machine direction MD by a tracking mechanism 215, as shown in FIG. 12. The belt 208 may comprise a first row of teeth 230 and a second row of teeth 232, as shown in FIG. 11, that may be used by the transmission mechanism 215 to move the belt, as shown in FIG. 12. The first row of teeth 230 may engage a first gear member 216 and the second row of teeth 232 may engage a second gear member 218. The surface profile of the first gear member 216 may match that of the first row of teeth 230 and the surface profile of the second gear member 218 may match that of the second row of teeth 232. More specifically, the first gear member 216 may comprise gear teeth 284 that correspond to the profile of the first row of teeth 230 and the second gear member 218 may comprise gear teeth 284 that correspond to the profile of the second row of teeth 232. Thus, as the axle member 220 rotates, the first gear member 216 and the second gear member 218 rotate about the longitudinal axle axis 224 of the axle member 220. As the first gear member 216 and the second gear member 188 rotate, the first gear member 216 and the second gear member 218 mesh with a portion of the first row of teeth 230 and the second row of teeth 232, respectively, to cause movement of the belt 208 across the deck surface 206 in the machine direction MD. By "mesh" is meant that the gear teeth of the gear member interlink with the row of teeth such that the gear teeth may exert a force on the row of teeth to move the belt.

As illustrated in FIG. 12, the transmission mechanism 215 may comprise an axle member 220 having a first end portion 248 and a second end portion 250, opposite the first end portion 248, and an axle length 252 extending in the cross direction CD. The axle member 220 may be adapted to rotate about the longitudinal axle axis 224. The axle member 220 may be connected to a roller 244 disposed between the first end portion 248 and the second end portion 250 of the axle member 220. The roller 244 engages the axle member such that when the axle member rotates, the roller also rotates about the longitudinal axle axis 224. The roller 244 has an outer surface 254 having a circumference and may be configured to support the belt 208 as it moves. Further, the roller 244 includes a first roller end 256 and a second roller end 258 opposite the first roller end. The first roller end 256 may be adjacent to the first gear member 216. Similarly, the second roller end 258 may be adjacent to the second gear member 218. More specifically, the second gear member 218 may be removably attached to the second roller end 258 and the first gear member 216 may be removably attached to the first roller end 256. For example, the second gear member 218 and the first gear member 216 may be screwed to the second roller end 258 and the first roller end 256, respectively. Further, at least one of the roller 244, the second gear member 218, and the first gear member 216 may be fixedly attached to the axle member 220 such that as the axle member rotates, the roller 244, the second gear member 218, and the first gear member 216 may also rotate about the longitudinal axle axis 224.

Further to the above, the belt 208 may be required to bend around the roller 244 and/or the first gear member 216 and the second gear member 218. The addition of one or more teeth to the second surface 212 of the belt 208 may result in the belt 208 becoming more difficult to bend around the gears 216, 218 and/or the roller 244. The rows of teeth 230 and 232 may be added to a belt 208 by an operation, which may include an adhesive, ultrasonic or thermal bond. More specifically, the rows of teeth 230, 232 may be attached to the second surface 212 of the belt 208. In an alternative embodiment, when bonding a first row of teeth and a second row of teeth 230 or 232 to a belt 208, a portion of the belt may be removed in the region of the first row of teeth 230 or the second row of teeth 232. Likewise, a portion of the angled row of teeth 230 and/or the straight row of teeth 232 may be removed. The tensile members of the belt and the first row of teeth 230 and/or the second row of teeth 232 may be in substantially direct contact. The tensile member may be removed partially or entirely.

However, despite the addition of the rows of teeth on the second surface of the belt, the first surface 210 of the belt including the portion of the angled row of teeth 230, straight row of teeth 232, and the distance therebetween, may be at substantially the same radial distance from the longitudinal axis 224 of the axle member 220. Stated another way, the first surface 210 of the belt 208 may remain substantially parallel to the longitudinal axis 224 of the axle member 220 as the belt 208 advances around the transmission mechanism 215. Similarly, the first surface 210 of the belt 208 may remain substantially parallel to the longitudinal shaft axis 268 as the belt 208 advances around the guide mechanism 246. Further, to allow for a small bend radius without excessive forces, the neutral axes of the portions of the belt 208 comprising the first row of teeth 230, second row of teeth 232, and the second surface 212 of the belt may be substantially the same, for example, within at least +/−1.0 mm and preferably less than +/−0.25 mm. Neutral axis refers here to the distance from the axis of revolution to a point at which a section of belt does not elongate or contract when bent.

The radius of roller section 244 may be chosen such that the roller surface 254 is in contact with the second surface 212 of the belt, and/or the neutral axis of the second surface 212 of the belt 208 may be substantially the same pitch diameter as the first row of teeth 230 and the second row of teeth 232. Pitch diameter for a geared belt is defined as a circle with a circumference equal to the number of gear teeth multiplied by the tooth pitch. Tooth pitch is the machine direction spacing between adjacent teeth. The pitch diameters of the first row of teeth 230 and the second row of teeth 232 may be substantially equal, although the tooth pitch may be unequal if a different number of teeth are chosen for the first row of teeth 230 and the second row of teeth 232. In view of the aforementioned, the first surface of conveyor belt 208 adjacent to an article may be substantially flat when the conveyor belt 212 is operationally engaged with and partially wraps around the transmission mechanism 215.

As previously stated, opposite the transmission mechanism 215 and adjacent to the second deck end 264 may be the guide mechanism 246, as shown in FIG. 4. The guide mechanism 246 may comprise a shaft 266 that may rotate about a longitudinal shaft axis 268, as illustrated in detail in FIG. 13. The shaft 266 may be configured to interact with the second surface 212 of the belt 208 and to guide and/or drive the belt 208 during operation of the conveyor 200. The shaft 266 includes an external surface 270 having a circumference and a shaft length 276 extending between a first shaft end 272 and a second shaft end 274, opposite the first shaft end 272. For example, in one embodiment, the shaft 266 may have an external surface 270 having a uniform circumference extending along the shaft length 276 from the first shaft end 272 to the second shaft end 274, not shown. In another alternative embodiment, the shaft 266 may have an external surface 270 having a circumference that varies along the shaft length 276.

Figure 13:
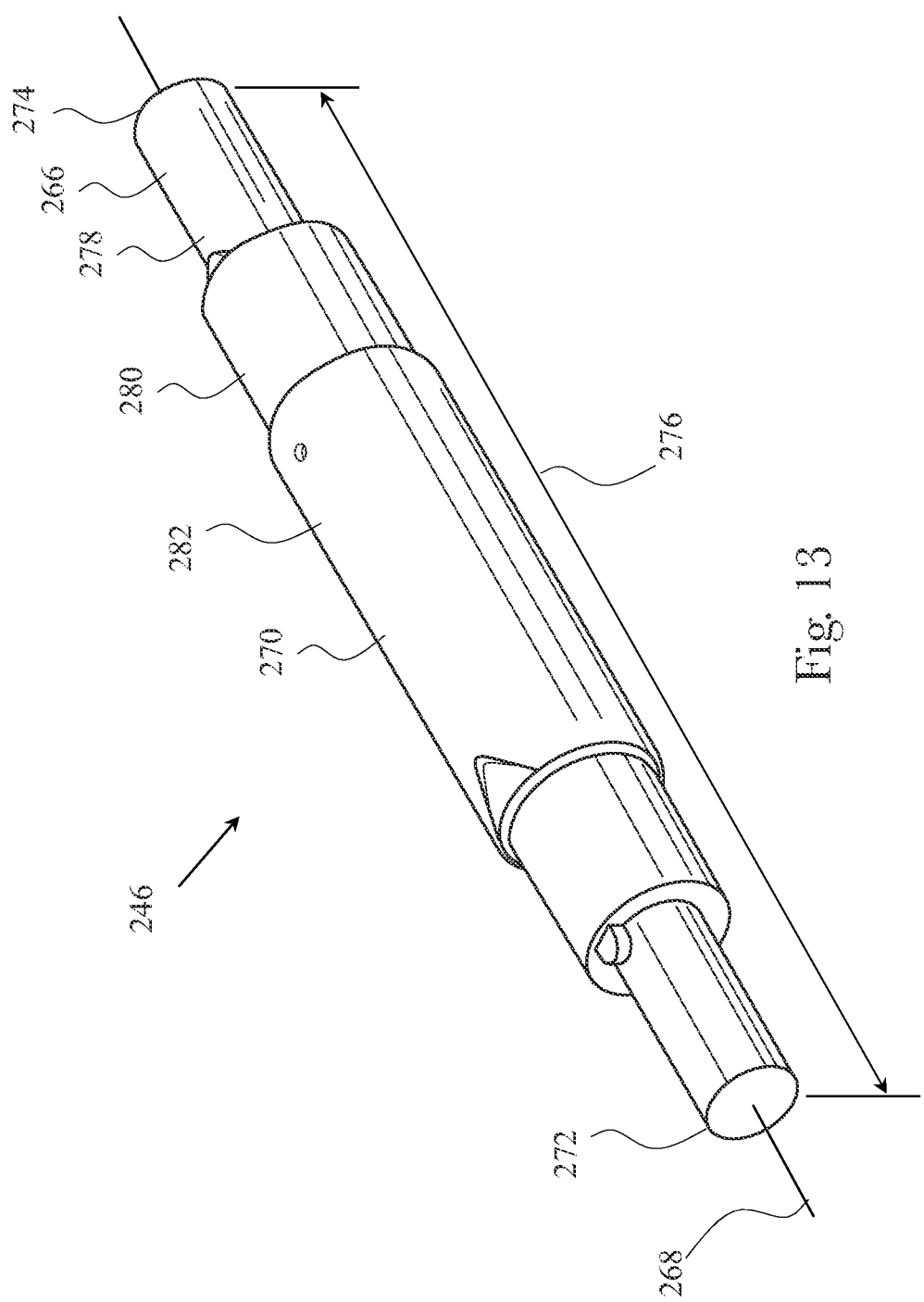
FIG. 13 is a perspective view of a guide mechanism in accordance with one non-limiting embodiment of the present disclosure.

For example, as shown in FIG. 13, the shaft 266 may have a first circumference 278 that is less than a second circumference 280 and a third circumference that may be greater than both the first circumference 278 and the second circumference 280. The difference in the second circumference 280 and the third circumference 282 may be based on the difference in height between the second surface 212 of the belt 208 having no teeth attached thereto and the height of the belt 208 having teeth attached thereto. Stated differently, the difference in the second circumference 280 and the third circumference 282 may be directly related to the tooth height 286, as shown in FIG. 9, of the row of teeth 230, 232. By varying the circumference of the shaft 266 to correspond to the different heights of the belt 208, the region of the belt 208 along the central longitudinal axis 234, not having teeth, may be supported by the shaft 266 having the third circumference 282 and the regions of the belt 208 having the first row of teeth 230 and the second row of teeth 131 may be supported by the shaft having the second circumference 280, which may be less than the third circumference 282. This allows the belt 208 to be supported and to help maintain alignment during the manufacturing process, which may be beneficial to both belt life and belt wear.

Further to the above, the shaft 266 may be machined such as to create an external surface 270 having one or more different circumference measurements. Alternatively, one or more cylindrical components may be attached to the shaft to create an external surface 270 having one or more different circumference measurements.

In another embodiment, not shown, the shaft 266 may comprise one or more gears having the same profile as the first row of teeth 230 and the second row of teeth 232. The shaft 266 may also comprise a roller connected to at least one of the first gear member 216 and the second gear member 218.

It is believed that the belt 208 can be advanced by either or both of the axle member 222 and the shaft 266. More specifically, a drive mechanism 222 may be operatively connected to at least one of the axle member 222 and the shaft 266. For example, in one embodiment, the drive mechanism 222 may be operatively connected to the axle member 222 such that the axle member 222 may be forced to rotate about the longitudinal axis 224, which in turn advanced the belt 208. In an alternative embodiment, the drive mechanism 222 may be operatively connected to the shaft 266 such that the shaft 266 may be driven to rotate around the longitudinal shaft axis 268, which in turn advances the belt 208.

In view of the aforementioned, a method for conveying absorbent articles may comprise the following steps. A conveyor 200, such as that shown in FIG. 4, may be provided. The conveyor 200 may comprise a deck 204 and a belt 208. The deck may include a channel 226. The belt 208 may include a first surface 210, a second surface 212 opposite the first surface, and a row of apertures 214. The second surface 212 of the belt 208 may be in a facing relationship with the deck 204. Air may be drawn through the channel 226 with a vacuum source 202. Further, absorbent articles may be placed on the first surface 210 of the belt 208. The air being drawn through the row of apertures 214 and the channel 226 may create suction on one or more absorbent articles which may hold the absorbent article against the first surface 210 of the belt 208. The belt 208 may be advanced in the machine direction MD. To aid in advancing the belt 208 and/or maintaining alignment of the belt 208, the angled teeth of a first gear member 216 may mesh with a first row of angled teeth connected with the second surface 212 of the belt 208, and the straight teeth of a second gear member 218 may mesh with a second row of straight teeth connected with the second surface 212 of the belt 208. The first gear member 216 and the second gear member 218 may be connected with an axle member 220. The row of apertures 214 may align with the channel 226 by moving the belt 208 in a cross direction CD. Further, the belt 208 may be guided in the machine direction MD by supporting the second surface 212 of the belt 208 with a shaft 266.

As previously mentioned, the apparatuses and methods according to the present disclosure may be utilized to advance and/or convey various types of absorbent articles through various types of process transformations during an assembly process. For example, the conveyor disclosed herein may be configured to operate in processes relating to the bi-fold of the chassis of a diaper pant. Further, the conveyor disclosed herein may also be used to transfer material into and/or out of a rotary unit operation. A rotary unit operation can include, for example, a final knife or inner chassis knife of a diaper pant converter, such as disclosed in U.S. patent application Ser. No. 13/616,478, filed Sep. 14, 2012. The conveyor herein may be configured for use as standard chassis conveyor, to transport between unit operation continuous webs and/or discrete products, such as an acquisition patch, a cuff, a continuous topsheet with discrete cores, a continuous backsheet with discrete ears and/or waistbands, or a continuous front ear web. Examples of processes that may be configured to operate with conveyors of the present disclosure are disclosed in U.S. Pat. No. 7,569,039; U.S. Patent Publication Nos. US2005/0107764A1; US2012/0061016A1; US2012/0061015A1; 2013/0255861A1; 2013/0255862A1; 2013/0255863A1; 2013/0255864A1; and 2013/0255865A1. Further still, the conveyor disclosed herein may be configured to operate in processes relating to opening or tucking first and second opposing side seams into a folded chassis of the diaper pant. Examples of such tucking process are disclosed in U.S. Patent Publication Nos. 2011/0251038 A1 and 2011/0247747 A1; and U.S. Pat. Nos. 6,723,035; 6,776,316; and 7,270,631. The conveyor herein may also be used to guide a web at an angle, such as for waist alignment conveyors which may track a web in the cross machine direction.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm." Every document cited herein, including any cross referenced or related patent or application, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A method for conveying absorbent articles, the method comprising the steps of:
    providing a conveyor comprising a deck and a belt, the deck including a channel, and the belt including a first surface, a second surface opposite the first surface, and a row of apertures, wherein the second surface is in a facing relationship with the deck;
    drawing air through the channel with a vacuum source;
    placing an absorbent article on the first surface of the belt;
    meshing angled teeth of a first gear member with a first row of angled teeth connected with the second surface of the belt, and meshing straight teeth of a second gear member with a second row of straight teeth connected with the second surface of the belt, wherein the first gear member and the second gear member are connected with an axle member;
    advancing the belt in a machine direction;
    aligning the row of apertures with the channel by moving the belt in a cross direction; and
    holding the absorbent article onto the belt by drawing air through the row of apertures;
    wherein the method comprises the further step of moving the second row of straight teeth in the cross direction relative to the straight teeth of the second gear member.

2. The method of conveying absorbent articles of claim 1, further comprising the step of guiding the belt in the machine direction by supporting the second surface of the belt with a shaft.

3. The method of conveying absorbent articles of claim 1, wherein the axle member further comprises a roller configured to support the second surface of the belt as the belt advances in the machine direction.

4. The method of conveying absorbent articles of claim 3, wherein the first gear member and the second gear member are removably attached to the roller.

* * * * *